United States Patent [19]

Horbaschek et al.

[11] Patent Number: 4,937,848
[45] Date of Patent: Jun. 26, 1990

[54] X-RAY EXAMINATION APPARATUS WITH REFERENCING SYSTEM FOR THE VIDEO DISPLAY

[75] Inventors: Heinz Horbaschek, Erlangen; Ulrich Bleitner, Ebersdorf, both of Fed. Rep. of Germany

[73] Assignee: Siemens Aktiengesellschaft, Berlin and Munich, Fed. Rep. of Germany

[21] Appl. No.: 343,739

[22] Filed: Apr. 27, 1989

[30] Foreign Application Priority Data

Jul. 28, 1988 [DE] Fed. Rep. of Germany ....... 3825709

[51] Int. Cl.$^5$ .............................................. H05G 1/64
[52] U.S. Cl. ....................................... 378/99; 358/111
[58] Field of Search ............................ 378/99; 358/111

[56] References Cited

U.S. PATENT DOCUMENTS 4,207,595  7/1980  Dittrich et al. .
4,674,107  6/1987  Urban ................................... 358/111

FOREIGN PATENT DOCUMENTS 0220501  9/1986  European Pat. Off. .
2194402  7/1973  France .

Primary Examiner—Craig E. Church
Attorney, Agent, or Firm—Hill, Van Santen, Steadman & Simpson

[57] ABSTRACT

An x-ray examination apparatus includes a position-adjustable x-ray tube, a patient support, and a position-adjustable image pick-up system, the image pick-up system including an x-ray image intensifier and a video camera coupled thereto. The output of the video camera is shown on a display monitor. Signals identifying the position of the x-ray tube and the image-pick-up system relative to a patient are supplied to a computer, which calculates angular deviation of those components from a desired reference. Signals corresponding to any such deviations are supplied to the horizontal and vertical sawtooth voltage generators for the video camera, so that scanning of the target of the video camera is always undertaken perpendicularly relative to the reference, independently of movement of the image pick-up system.

9 Claims, 4 Drawing Sheets

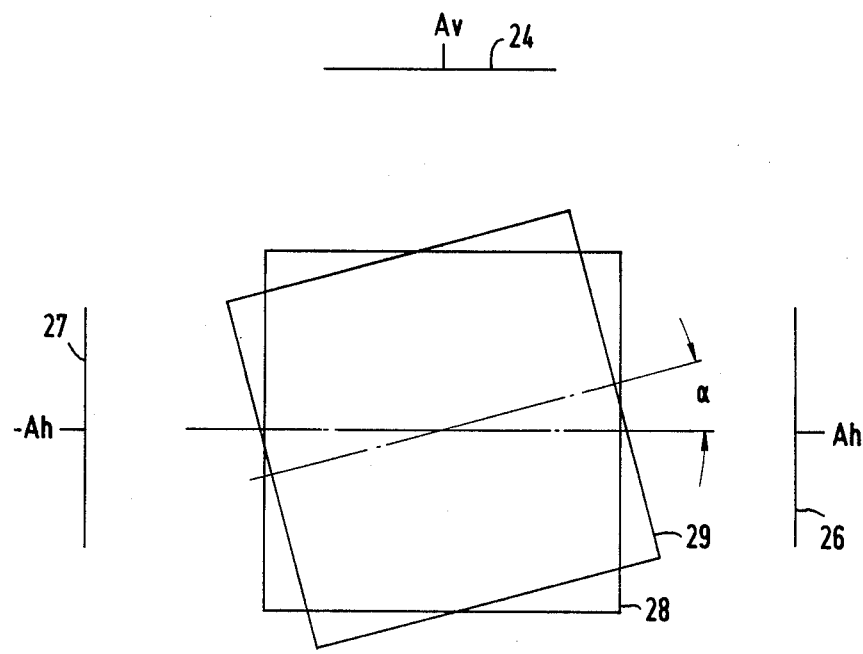
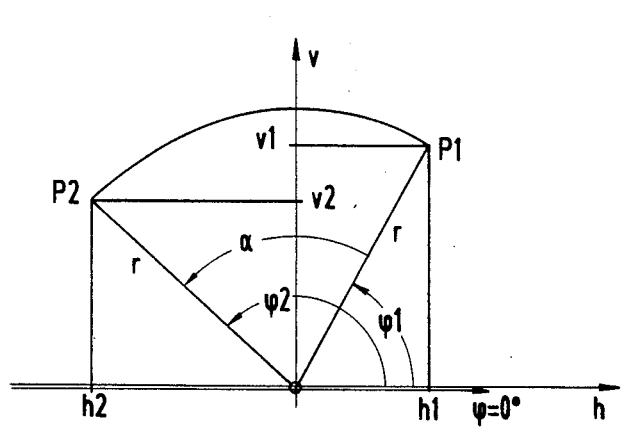
FIG 2
FIG 3

X-RAY EXAMINATION APPARATUS WITH REFERENCING SYSTEM FOR THE VIDEO DISPLAY

BACKGROUND OF THE INVENTION

Field of the Invention

The present invention is directed to an x-ray apparatus for producing x-ray images of a patient, and in particular to such an x-ray apparatus having a positionadjustable x-ray tube, a patient support, and a positionadjustable pick-up system, with the image pick-up system including an x-ray image intensifier and a video camera coupled thereto, the output of the video camera being supplied to an image reproduction system for display.

Description of the Prior Art

An x-ray diagnostics installation is described in German No. OS 3 536 079 (corresponding to U.S. application Ser. No. 289,429 filed Dec. 23, 1988, which is a continuation of application 912,041 filed Sept. 24, 1986 (now abandoned), assigned to the same assignee as the present application and naming Heinz Kresse as inventor) wherein the system components, namely the x-ray tube the patient support, and image pick-up system, are mounted on robot arms so that component can be independently threedimensionally adjusted. In this known system, however, the video camera of the image pick-up system is arbitrarily aligned relative to other components, so that alignment of the resulting x-ray image to given conditions, such as a given reference, cannot be undertaken. It is important, however, for the physician to have the image shown on the display monitor to be in a position which he or she expects as an observer due to his or her position relative to the patient. In other words, it is undesirable for the physician to have to mentally translate the image displayed on the monitor to coincide approximately with his or her actual view of the patient. The most common translation of the image which must be undertaken in conventional systems is to rotate the image around the axis of a central ray of the x-ray tube.

SUMMARY OF THE INVENTION

It is an object of the present invention to provide an x-ray apparatus having an independently movable, or co-movable, x-ray source and image pick-up system wherein an automatic correction is undertaken in the displayed image for rotation of the apparatus around the axis of a central ray of the x-ray source.

The above object is achieved in accordance with the principles of the present invention in an x-ray examination apparatus including means for acquiring the position of a reference system and means connected to the means for acquiring the position of the reference system which calculates an angle-dependent superimposition of the deflection voltages which are to be used for the video camera. The signals corresponding to the deviation from the reference are supplied to deflecting stages for video camera, which controls scanning of the target of the video camera so as to maintain alignment of the reference system with the central ray independently of the rotation of the image pickup system. The position of the reference system is recognized with the signal acquiring means, and an evaluation of this position and a superimposition of the horizontal and vertical deflecting voltages for the video camera is undertaken with a computer, so that the deflection of the video camera always ensues so that the scanning direction is perpendicular relative to the desired position of the x-ray image, for example relative to the alignment of the reference system.

Given a stationary x-ray examination apparatus, the necessary correction can be undertaken automatically by the use of position transmitters arranged on at least one of the system components, these position transmitters identifying the rotary angle of the image pick-up system relative to the reference system, and supplying a signal to a computer. On the basis of the signal from the position transmitters, which need only be connected, for example, to the image pick-up system, if the reference system is rigidly fixed, the computer calculates the rotational angle of the image pick-up system relative to the alignment of the reference system, for example a patient support. Use of the patient support as a reference system simplifies the necessary calculations.

It is also possible to provide a reproduction of the x-ray image in the position at which an examining physician would expect the image, due to the position of that person relative to the patient. In this case, the reference system is the alignment of the examining physician relative to the x-ray system, and an input means is provided for entering the position of the examining person in the computer. The computer then again calculates an angle between the reference position for controlling deflection units for operating the video camera relative to the central beam of the x-ray tube.

The computer may include a first stage in which the angle is identified based on the signals from the position transmitters, a signal corresponding to this angle then being supplied to a stage which calculates the sine and cosine of this angle. The outputs of the sine and cosine forming stage are supplied to a plurality of multiplier. Certain of the multiplier are supplied with the horizontal sawtooth voltage signal which is to be used to control the operation of the video camera, and certain other ones of the multipliers are supplied with the vertical sawtooth voltage generator for the video camera. The outputs of the multipliers are then selectively combined and respectively supplied to a horizontal deflection stage and a vertical deflection stage, which respectively adjust the horizontal and vertical sawtooth voltages to maintain alignment with the reference system.

An arbitrary adjustment of the x-ray image can also be undertaken for use in a mobile x-ray apparatus by providing means for mixing a mark into the x-ray image which is used the reference system. The mark generator and positioner is connected between the video camera and the image reproduction system (television monitor). The position of the mark is also supplied to the computer. It is also possible to mix two marks into the x-ray image, with one of the marks identifying the reference system, and the other mark identifying the position of the reference system. Adjustment is simplified if the mark which is mixed in the x-ray image identifies the desired position, and it is assumed that the perpendicular on the television monitor is the reference system.

DESCRIPTION OF THE DRAWINGS

FIGS. 2 and 3 show geometrical relationships during scanning for explaining the operation of the apparatus of FIG. 1.

DESCRIPTION OF THE PREFERRED EMBODIMENTS

Figure 1:
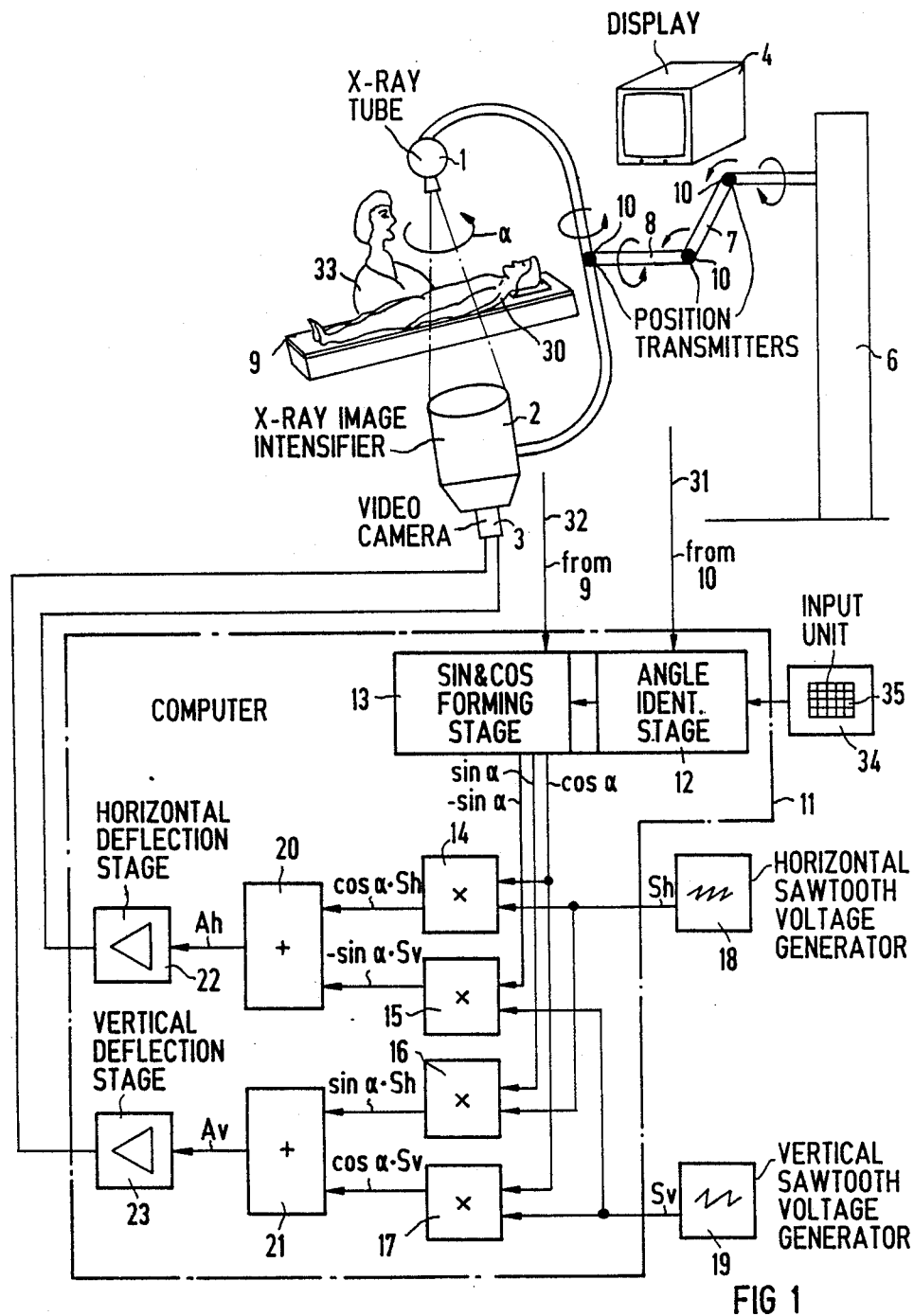
FIG. 1 is a schematic diagram of an x-ray examination apparatus constructed in accordance with the principles of the present invention.

An x-ray apparatus constructed in accordance with the principles of the present invention is shown in FIG. 1, and includes an x-ray tube 1, an image pick-up system consisting of an x-ray image intensifier 2 and video camera 3, and an image reproduction system which includes a television monitor 4, connected to an output (not shown in FIG. 1) of the video camera 3. The x-ray tube 1 and the x-ray image intensifier 2, with the video camera 3 coupled thereto, are connected by a C-bend 5. These components, may, however, alternatively be separately suspended by robot arms as shown in the aforementioned German OS No. 3 536 079. The C-bend 5 is attached to a pedestal 6 in rotatable and pivotable fashion by a robot arm. The robot arm includes a first lever 7 attached to the pedestal 6 in rotatable and pivotable fashion, and having a free end pivotably connected to a second lever 8 to which the C-bend 5 is mounted in rotatable and pivotable fashion.

A patient support 9, on which a patient 30 can lie, is disposed between the x-ray tube 1 and the x-ray intensifier 2. For simplicity, it will be assumed in this embodiment that the patient support 9 has a fixed, invariable alignment relative to the pedestal 6. This is, however, not necessary, and the patient support 9 may be mounted in a freely mobile fashion by robot arm.

Each articulation of the robot arm consisting of the levers 7 and 8 is provided with a position transmitter 10, each position transmitter having an output which is supplied via a line 31 to a computer 11. If the patient support 9 were also mounted of a robot arm, that robot arm would also have one or more position transmitters, whose outputs would also be supplied to the computer 11 on line 31.

The computer 11 includes an angle identification stage 12, which identifies the rotational angle $\alpha$ from the outputs of the position transmitters 10. The corresponding sine and cosine functions sine $\alpha$ $-\sin \alpha$ and $\cos \alpha$ are formed from these values of the angle $\alpha$ in a second stage 13. The functions $\sin \alpha$, $-\sin \alpha$ and $\cos \alpha$ are supplied to four multiplication stages 14, 15, 16 and 17. The output Sh of a horizontal sawtooth voltage generator 18 for the video camera 3 is respectively multiplied by $\cos \alpha$ and $\sin \alpha$ in multiplier 14 and 16. The output Sv of a vertical sawtooth voltage generator 19 for the video camera 3 is respectively multiplied by $-\sin \alpha$ and $\cos \alpha$ in multiplier 15 and 17. The outputs of the multiplication stages 14 and 15 are combined in an adder 20, and the outputs of the multipliers 16 and 17 are combined in an adder 21. The output Ah of the adder 20 is supplied to a horizontal deflection stage 22, and the output Av of the adder 21 is supplied to a vertical deflection stage 23. The outputs of both deflection stages 22 and 23 are supplied to the scan beam deflection system (shown in FIG. 2) of the video camera 3.

As a result of the aforementioned selective multiplication in the stages 14 through 17, the deflection stages 22 and 23 respectively receive the horizontal and vertical sawtooth voltages multiplied by the cosine and sine functions, with the voltage which is multiplied by the sine for supply to one of the deflection stages being multiplied by the cosine for supply to the other deflection stage.

The geometrical relationship during scanning of an image by the electron beam in the video camera 3 will be described in greater detail with reference to FIG. 2. As is generally standard, the scanning system of the video camera 3 may be a magnetic system, with deflection coils (not shown) generating a corresponding deflection field which acts on the electron beam. As shown in FIG. 2, however, the deflection may also ensue electrostatically, with the corresponding deflection voltages Ah and Av from the deflection stages 22 and 23 being supplied to respective deflection plates 24, 25, 26 and 27. The first square 28 indicates a standard screen position when horizontal and vertical sawtooth voltages with zero deflection are supplied to the plates. When a deflection such as rotation by the angle $\alpha$ in comparison to the first square 28 is to be undertaken, so as to translate or re-orient the original image to the position indicated by the square 29, deflection voltages must be supplied to cause deflection of the electron beam of the video camera 3 in a direction perpendicular to the sides of the square 29. The required deflection voltages Ah and Av can be mathematically calculated for an arbitrary rotational angle $\alpha$ in the following manner.

As shown in FIG. 3, an arbitrary point P1 having rectangular coordinates h1 and v1 and polar coordinates r and $\phi1$, is to be translated through the angle $\alpha$ to point P2, having rectangular coordinates h2 and v2 and polar coordinates r and $\phi2$. The translation takes place along a circular arc having a radius r. The following relationships are then valid:

$$h1 = r \cdot \cos \phi1 \qquad (1)$$
$$h2 = r \cdot \cos \phi2 \qquad (2)$$
$$v1 = r \cdot \sin \phi1 \qquad (3)$$
$$v2 = r \cdot \sin \phi2 \qquad (4)$$

As can be seen from FIG. 3, $\phi2 = \phi1 + \alpha$, so that:
$$h2 = r \cos (\phi1 + \alpha)$$
$$v2 = r \sin (\phi1 + \alpha)$$

The relationships for the cosine and the sine of two added angles are:

$$\cos (\phi + \alpha) = \cos \phi \cdot \cos \alpha - \sin \phi \cdot \sin \alpha$$

$$\sin (\phi + \alpha) = \sin \phi \cdot \cos \alpha + \cos \phi \cdot \sin \alpha$$

Therefore:

$$h2 = r \cos \phi1 \cdot \cos \alpha - r \sin \phi1 \cdot \sin \alpha$$

$$v2 = r \sin \phi1 \cdot \cos \alpha + r \cos \phi1 \cdot \sin \alpha$$

Substituting equations (1) and (3) in the two equations immediately above yields:

$$h2 = h1 \cos \alpha - v1 \sin \alpha$$

$$v2 = v1 \cos \phi + h1 \sin \alpha$$

Because the point P1 represents an arbitrary in the square 28, and deflection can be undertaken according to the video screening, the following general deflection functions for the deflection voltage associated with the square 29 result:

$$Ah = \cos \alpha \, Sh - \sin \alpha \, Sv$$

$$Av = \cos \alpha \, Sv + \sin \alpha \, Sh.$$

In the above example, the patient support 9 was selected as the reference system, so that the angle α between the alignment of the patient support 9 and the alignment of the vertical deflection of the video camera 3 was to be calculated. Information from which the angle α can be identified was supplied via the line 31. The position of the C-bend 5 was supplied to the computer 11 via a further line 32, indicating whether the system is operating in an under-table or above-table mode. The computer 11 undertakes the calculation of the corresponding functions from these values.

In some instances, however, it is preferable that the line of sight of an examining person 33 onto the patient 30, and thus onto the central ray of the x-ray tube 1, be used as the reference system instead of the patient support 9. For this purpose, an input unit 34 is connected to the computer 11, with the position of the examining person 33 being supplied to the angle identification stage 12 via the input unit 34. After entry of the position, such as by coordinates entered via a keyboard 35, the angle identification stage 12 calculates the orientation of a line between the position of the person 33 and the central ray of the x-ray tube 1, and then calculates the angle α between this line and the respective alignment of the x-ray apparatus on the basis of the outputs of the position transmitters 10.

The x-ray apparatus described above thus undertakes an automatic electronic correction of the apparatus rotation so that the x-ray image is always displayed on the monitor 4 with the desired alignment.

Figure 4:
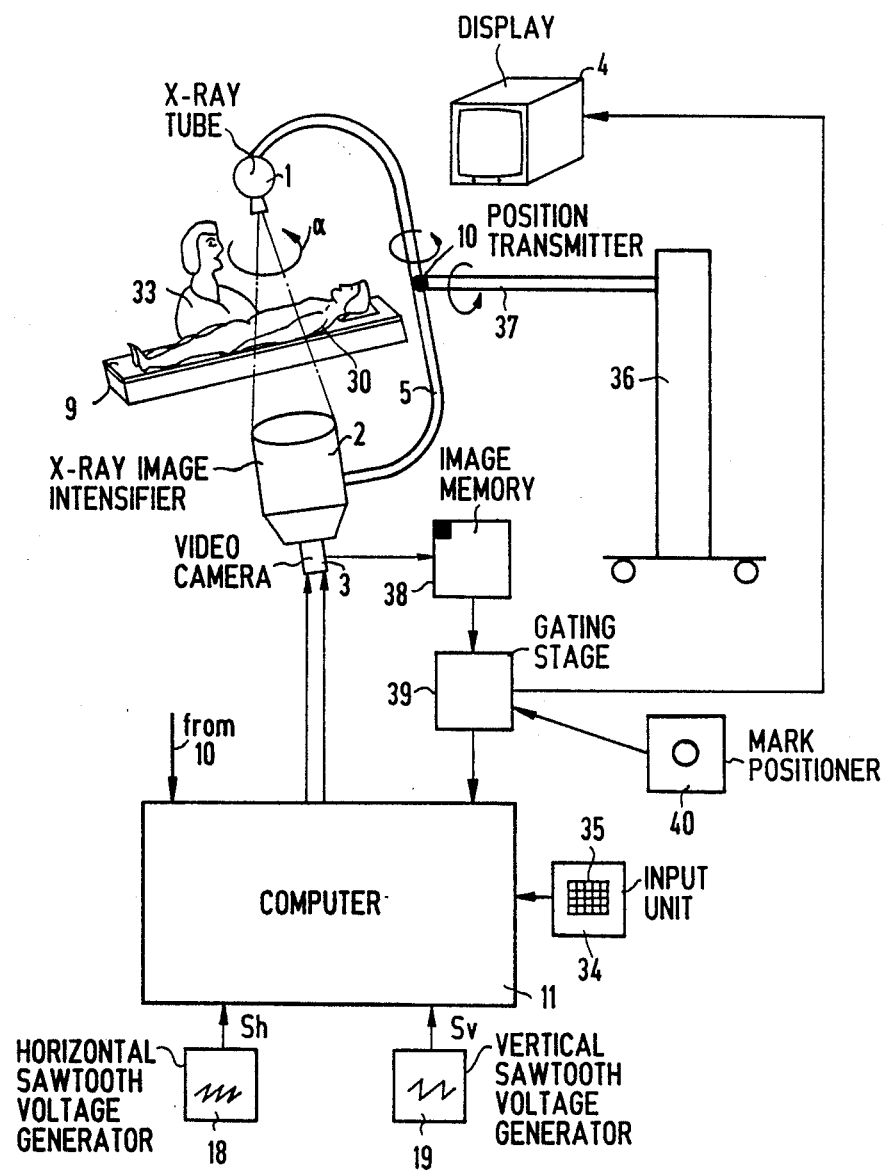
FIG. 4 is a schematic diagram of a further embodiment of an x-ray examination apparatus constructed in accordance with the principles of the present invention.

A further embodiment of the invention is shown in FIG. 4 for a displaceable, mobile x-ray apparatus 36. Components corresponding to those already identified in connection with FIG. 1 has the same reference numerals. In this embodiment, the C-bend 5 is secured to the movable apparatus 36 via a bracket 37. The connection between the bracket 37 and the C-bend 5 is articulated permitting rotational and pivoting of the C-bend 5, with the articulation being provided with a position transmitter 10.

An image memory 38 for the x-ray images and a gating stage 39 mix one of more marks into the video image (as described in greater detail below). The image memory 38 and gating stage 39 are connected between the video camera 3 and the display 4. The position of the marks can be varied by a mark positioner 40. Either the mark positioner 40 of the gating stage 39 is connected to the computer 11 so that the computer 11 is supplied with the position of the marks. The computer then undertakes the calculations described above for the video camera 3 based on the mark position.

Examples related to the embodiment shown in FIG. 4 are set forth in greater detail with reference to FIGS. 5 through 8. All of those figures show a schematic representation of an x-ray image of a human leg 41 with bones 42 and 43 and the knee-cap 44.

Figure 5:
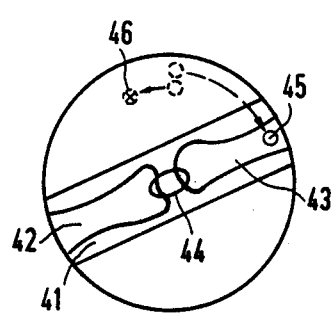
FIGS. 5 through 8 are schematic reproductions of displayed images for explaining the operation of the embodiment shown in FIG. 4.

FIG. 5 shows the output image in a basic position, without rotation of the x-ray image, such as, for example, may have been entered in the image memory 38 following a first exposure. A first mark 45 is placed at prominent position in the x-ray image, for example on the leg 41, with the mark positioner 40, so that this first mark 45 can be used as a reference system.

Figure 6:
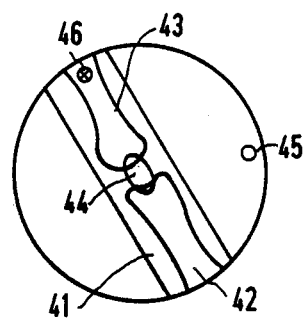
Figure 7:
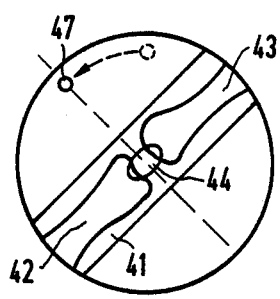
Figure 8:
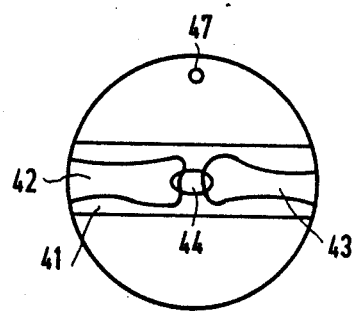

The position of a second mark 46 is then adjusted so that the position of the second mark 46 corresponds to the desired position for viewing of the image, i.e., the position to which the reference system image is to translated. The computer 11 then calculates the required deflection based on the angle which the two marks 45 and 46 make with each other, so that the x-ray image shown on the display 4 is situated in the desired position when the x-ray apparatus 36 is again switched on, as shown in FIG. 6.

If, for example, the vertical alignment in the x-ray image is selected as the reference system, only one mark 47 need be employed, instead of two marks. The mark 47 is positioned using the mark position or 40, and the computer 11 calculates the angle of the new position of the mark 47 relative to the reference direction, and calculates the required deflection therefrom. This results in the image being re-aligned from the position shown in FIG. 7 to the position shown in FIG. 8 when the x-ray system is again switched on.

Although modifications and changes may be suggested by those skilled in the art, it is the intention of the inventors to embody within the patent warranted hereon all changes and modifications as reasonable and properly come within the scope of their contribution to the art.

We claim as our invention:

1. An x-ray examination apparatus comprising:
   an x-ray tube;
   an image pick-up system including an x-ray image intensifier coupled to a video camera, said video camera having a scanning beam deflection system having a scan direction;
   a patient support disposed between said x-ray tube and said image pick-up system adapted to support a patient so that x-radiation from said x-ray tube is attenuated by said patient and said image pick-up system thereby forms an x-ray image of said patient;
   means for adjusting the position of said x-ray tube and said image pick-up system;
   means for displaying said x-ray image from said image pick-up system;
   means for identifying a reference system;
   means for generating information identifying the position of the reference system; and
   means for controlling said scanning beam deflection system of said video camera dependent on said position of said reference system so that said scan direction of said video camera is always aligned with said reference system independently of the position of the x-ray tube and the image pick-up system.

2. An x-ray examination apparatus as claimed in claim 1, wherein said means for adjusting includes a plurality of position transmitters, said position transmitters each supplying a signal to said means for controlling said scanning beam deflection system.

3. An x-ray examination apparatus as claimed in claim 1, wherein said means for controlling said scanning beam deflection system is a means for rotating said x-ray image perpendicularly relative to the alignment of said reference system.

4. An x-ray examination apparatus as claimed in claim 1, wherein said means for identifying a reference system is a means for identifying said patient support as said reference system.

5. An x-ray examination apparatus as claimed in claim 1, wherein said means for identifying a reference system is an input means for entering a position of an attendant in said means for controlling said scanning beam deflection system so that said reference system is the alignment of said attendant relative to a central x-ray beam from said x-ray tube.

6. An x-ray examination apparatus as claimed in claim 1 further comprising a horizontal sawtooth voltage generator and a vertical sawtooth voltage generator for said video camera, and wherein said means for generating information comprises:

means for assigning an angle value to the position of the x-ray tube and the image pick-up system relative to said reference system;

means for forming the sine and the cosine of said angle value;

multiplier means for multiplying the horizontal sawtooth voltage from the horizontal sawtooth voltage generator and the vertical sawtooth voltage from the vertical sawtooth voltage generator by each of said sine and cosine of said angle value;

first combining means for subtracting the sine of said angle value multiplied by said vertical sawtooth voltage from the cosine of said angle value multiplied by the horizontal sawtooth voltage to obtain an output;

horizontal deflection means, supplied with said output of said first combining means, for controlling horizontal deflection in said scanning beam deflection system;

second combining means for adding the sine of said angle value multiplied by said horizontal sawtooth voltage with the cosine of said angle value multiplied by said vertical sawtooth voltage to obtain an output; and vertical deflection means, supplied with the output of said second combining means, for controlling vertical deflection in said scanning beam deflection system.

7. An x-ray examination apparatus as claimed in claim 1, wherein said means for identifying a reference system is a means for mixing a mark into said x-ray image on said means for displaying and wherein said means for generating information is a means for forming a signal of the position of the mark.

8. An x-ray examination apparatus as claimed in claim 7, further comprising means for mixing a further mark into said x-ray image on said means for displaying, said mark identifying said reference system and said further mark identifying a position of said reference system.

9. An x-ray examination apparatus as claimed in claim 7, wherein said means for identifying a reference system is a means for identifying the vertical on said x-ray image of said means for displaying as said reference system, and further comprising means for mixing a mark into said x-ray image for identifying a desired position to which said x-ray image is to be aligned.

* * * * *